United States Patent [19]  [11] 4,190,827
Diamond  [45] Feb. 26, 1980

[54] MULTICHANNEL SALINITY METER
[75] Inventor: Joseph M. Diamond, Brooklyn, N.Y.
[73] Assignee: McNab, Incorporated, Mount Vernon, N.Y.
[21] Appl. No.: 943,801
[22] Filed: Sep. 19, 1978

Related U.S. Application Data

[63] Continuation of Ser. No. 687,613, May 18, 1976, abandoned.
[51] Int. Cl.² .................... G08B 23/00; G01N 27/42; G01R 27/02
[52] U.S. Cl. .................................... 340/500; 340/501; 324/65 R; 324/439; 324/62
[58] Field of Search ............... 340/500, 501, 506, 510, 340/514, 588, 589, 599, 181; 324/30 R, 62 R, 65 R

[56] References Cited

U.S. PATENT DOCUMENTS

| | | | |
|---|---|---|---|
| 3,131,346 | 4/1964 | Parke | 324/30 |
| 3,166,678 | 1/1965 | Fleshman | 307/351 |
| 3,491,287 | 1/1970 | Brown | 324/30 A |
| 3,559,193 | 1/1971 | Savaglio | 340/662 |
| 3,757,205 | 9/1973 | Dauphinee | 324/30 R |
| 3,771,548 | 11/1973 | Rauchwerger | 340/235 |
| 3,946,309 | 3/1976 | Roughton et al. | 324/30 R |
| 3,965,414 | 6/1976 | Teass, Jr. | 324/30 R |
| 3,992,662 | 11/1976 | Koepnick et al. | 324/30 R |

Primary Examiner—John W. Caldwell, Sr.
Assistant Examiner—Donnie L. Crosland
Attorney, Agent, or Firm—Peck & Peck

[57] ABSTRACT

A multichannel salinity meter combines a semi-squarewave signal with a peak actuated detector to develop a salinity signal proportional to conductivity. Each salinity channel includes a separate presettable alarm level and alarm indicators provided by a blinking lamp at the salinity module, local and remote bells and a remote lamp. a bell cutout switch is provided to optionally silence the local and remote bell indicators. Each salinity channel provides a dump signal which may be used to control a dump valve whereby any alarm condition causes dumping of the water in the alarm channel. A test signal available to each salinity channel provides the instrument with a test mode.

9 Claims, 6 Drawing Figures

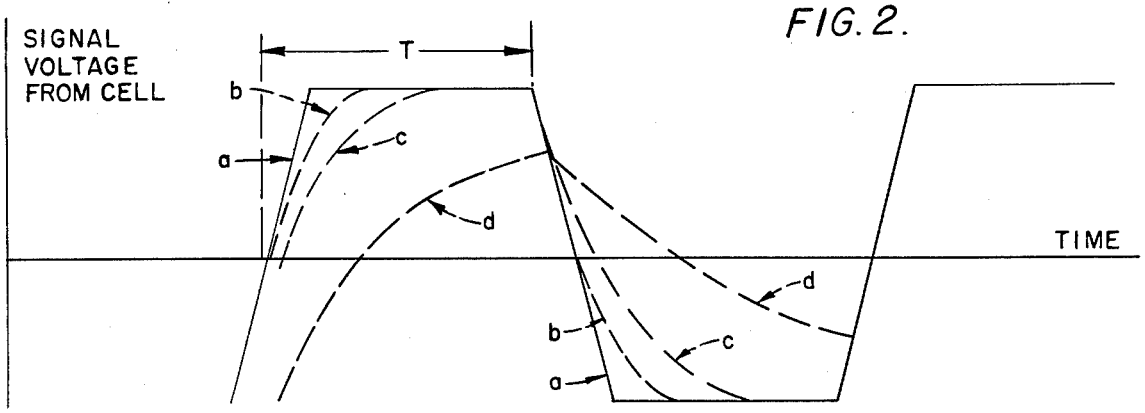

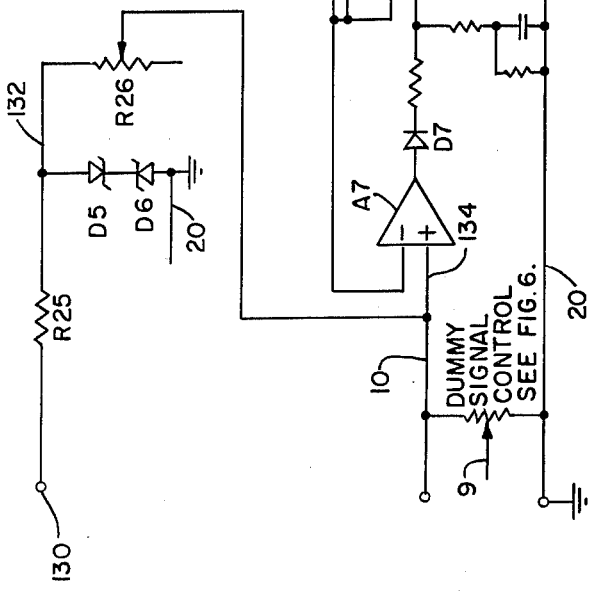
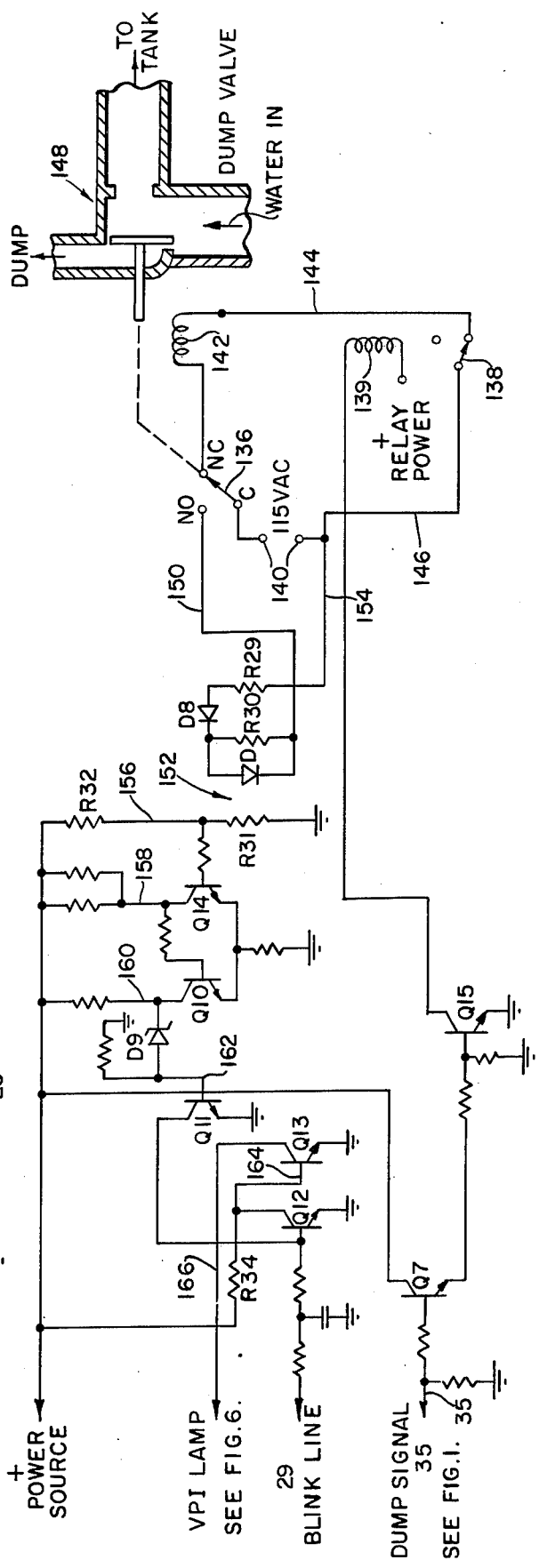
FIG. 4.
FIG. 5.

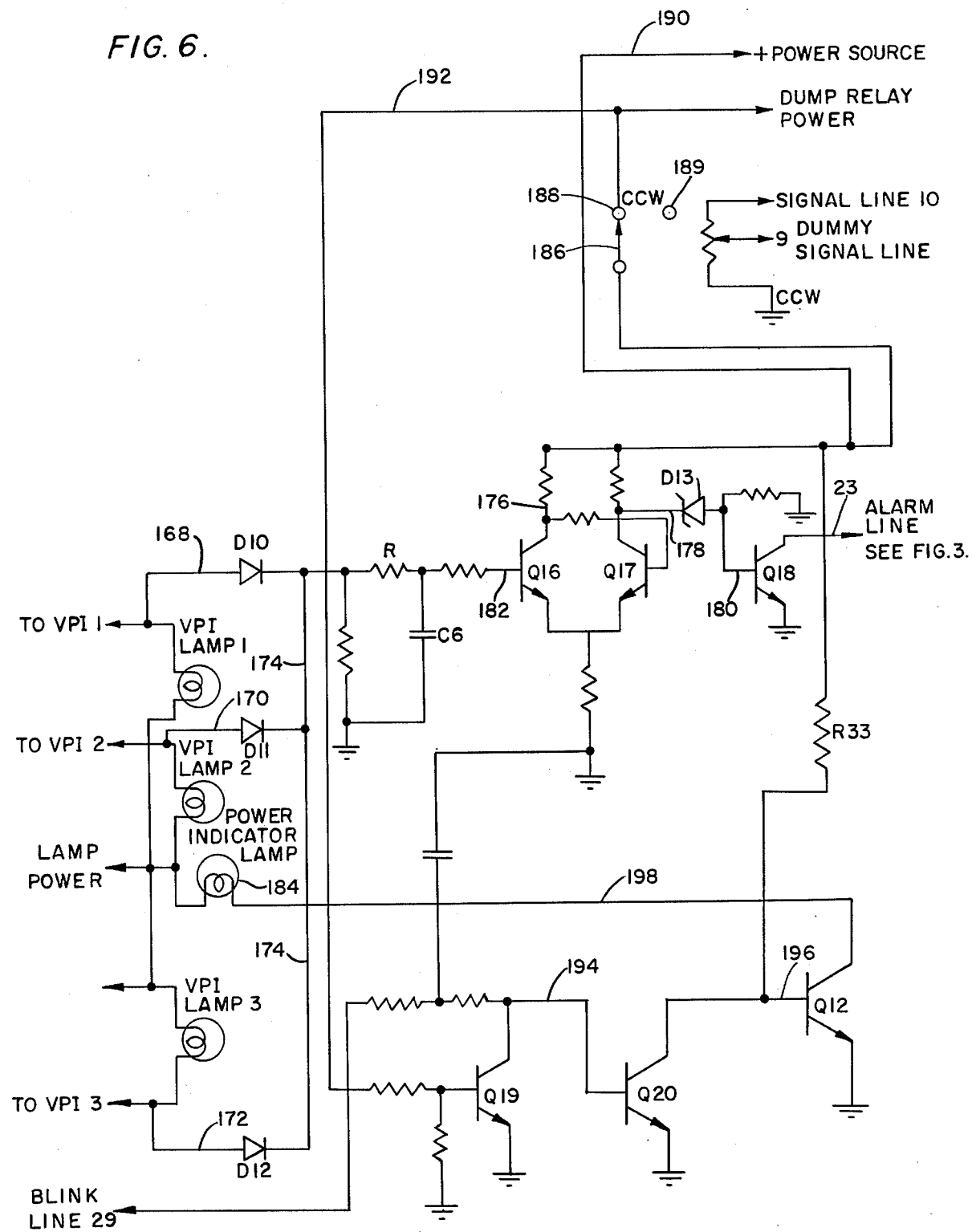

MULTICHANNEL SALINITY METER

This is a continuation, of application Ser. No. 687,613 filed May 18, 1976, now abandoned.

BACKGROUND OF THE INVENTION

The present invention relates generally to monitoring systems and, more particularly, to a system useful for measuring the salinity of solutions.

SUMMARY OF THE INVENTION

The present invention relates to a system for measuring the concentration of salts, or other dissolved solutes, in a solution by measuring the electrolytic conductivity of the solution while correcting for changes in the solution temperature.

A feature of the present invention is a very high input impedance at the measuring input, enabling the system to be used with a variety of measuring conductivity cells.

Another feature of the present invention is the use of a semi-square-wave measuring signal with a peak actuated detector, making the system highly independent of the effects of cable capacitance.

Another feature of the present invention is the use of an individual alarm indicator for each channel, thereby providing each channel with a preset, changeable alarm level. The alarm indication is given by the blinking of a lamp on the salinity module, by the actuation of local and/or remote bells, and by the lighting of a remote lamp. A bell cutout switch is provided whereby the local and remote bells may be silenced. When the switch is in the cutout position and an alarm condition occurs, the alarm lamp indication is modified from blinking to constant on and, if the excess salinity condition which resulted in the alarm condition should disappear, the indicator reverts to a blinking mode. This provides a reminder to the operator to throw the switch back to the normal position so that the lamp is fully extinguished when, and only when, there is no alarm condition.

Another feature of the present invention is the use of a dump valve and dump lamp, whereby an impure water condition causes dumping of the impure water and the activation of a dump lamp indicator. Each dump valve is controlled by a salinity module by means of a relay located in the module. When a salinity module associated with a dump valve detects an alarm condition indicating excessive impurity in the water stream in question, the associated relay cuts off power to the solenoid dump valve, causing the valve to open and dump the impure water. When such a dump condition occurs, a dump lamp, which is normally continuously illuminated, is caused to blink until the solenoid dump valve is manually reset. Manual resetting is required because the solenoid dump valve locks itself (by breaking the electrical circuit) in the dumping position. Consequently, the salinity module loses control over the dump valve once it starts to dump, even though the alarm condition which originally caused the dump may have disappeared. The blinking of the dump lamp is controlled by a return signal from the dump valve circuit and, therefore, always indicates the true state of the dump valve.

Another feature of the present invention is the use of a read meter switch in each salinity module, whereby the output from that module can selectively be connected to a common meter to indicate the momentary salinity in that channel.

Another feature of the present invention is the capability of selectively providing a dummy or test signal to each salinity module, whereby the alarm setting of each module may be set or checked against a scale. Each module has a dummy signal switch whereby the output signal from the conductivity cell is replaced by a dummy test signal from a manually controlled dummy signal potentiometer. The dummy signal permits the meter to be deflected to any point on its scale and thus permits the alarm setting of the salinity module to be checked against the scale and altered if desired. The dummy signal potentiometer is combined with a switch that interrupts the power supply to the dump relays when the potentiometer is turned to the operating portion of its range. The purpose of this circuit is to prevent a dump initiation during testing. To remind the instrument operator that dump operation is thus inhibited, a power lamp on the instrument is caused to blink so long as the test condition exists. This feature can also be used to intentionally inhibit dumping during periods of emergency operation. Although dumping will be disabled, salinity reading and alarm indication will be normal.

The present invention is summarized in that a multichannel salinity meter includes a design which provides a high input impedance at the measuring input; a semi-square-wave measuring signal and a peak actuated detector combine to make the instrument practically unaffected by cable capacitance; each salinity channel includes a separate presettable alarm level and an alarm indication; alarm indications are provided by a blinking lamp at the salinity module, by local and/or remote bells and by the lighting of a remote lamp; a bell cutout switch is provided to optionally silence the local and remote bell indicators; when the cutout switch is in the cutout position, the alarm lamp indication is modified from a blinking mode to a continuously on mode; each salinity module may control a dump relay and a dump valve whereby, when an alarm condition occurs, the dump valve is deenergized to cause the impure water to be dumped; dump situations are indicated by lamps which, though normally continuously on, are caused to blink during dumping and until the dump valve is manually reset; a read meter switch on each salinity module combines with a common meter to provide a reading of the momentary salinity in any channel; a dummy signal switch at each salinity module enables a dummy or test signal to be applied to the module for setting and/or changing the alarm level setting of the module; the dummy signal switch is combined with another switch which interrupts power to the dump relay so that a dump initiation is prevented during module calibration or testing; a lamp, which is normally continuously on, is caused to blink during periods of testing when the dump operation is inhibited; and the dummy signal switch connections can be used to intentionally inhibit dumping during periods of emergency operation, although the salinity reading and alarm indication functions of the instrument will be unaffected.

BRIEF DESCRIPTION OF THE DRAWINGS

FIG. 2 illustrates a semi-square-wave and several distorted versions of the wave caused by different valves of capacitance;

FIG. 3 is a partial block-schematic diagram illustrating the interconnection between the salinity module and the bell and alarm relay circuits;

FIG. 4 is a schematic diagram of the reference voltage circuits;

FIG. 5 is a partial schematic diagram of the valve position indicator circuit; and FIG. 6 is a schematic diagram of the valve position indicator lamp circuit, alarm latch circuit and power lamp circuit.

DESCRIPTION OF THE PREFERRED EMBODIMENT

Figure 1:
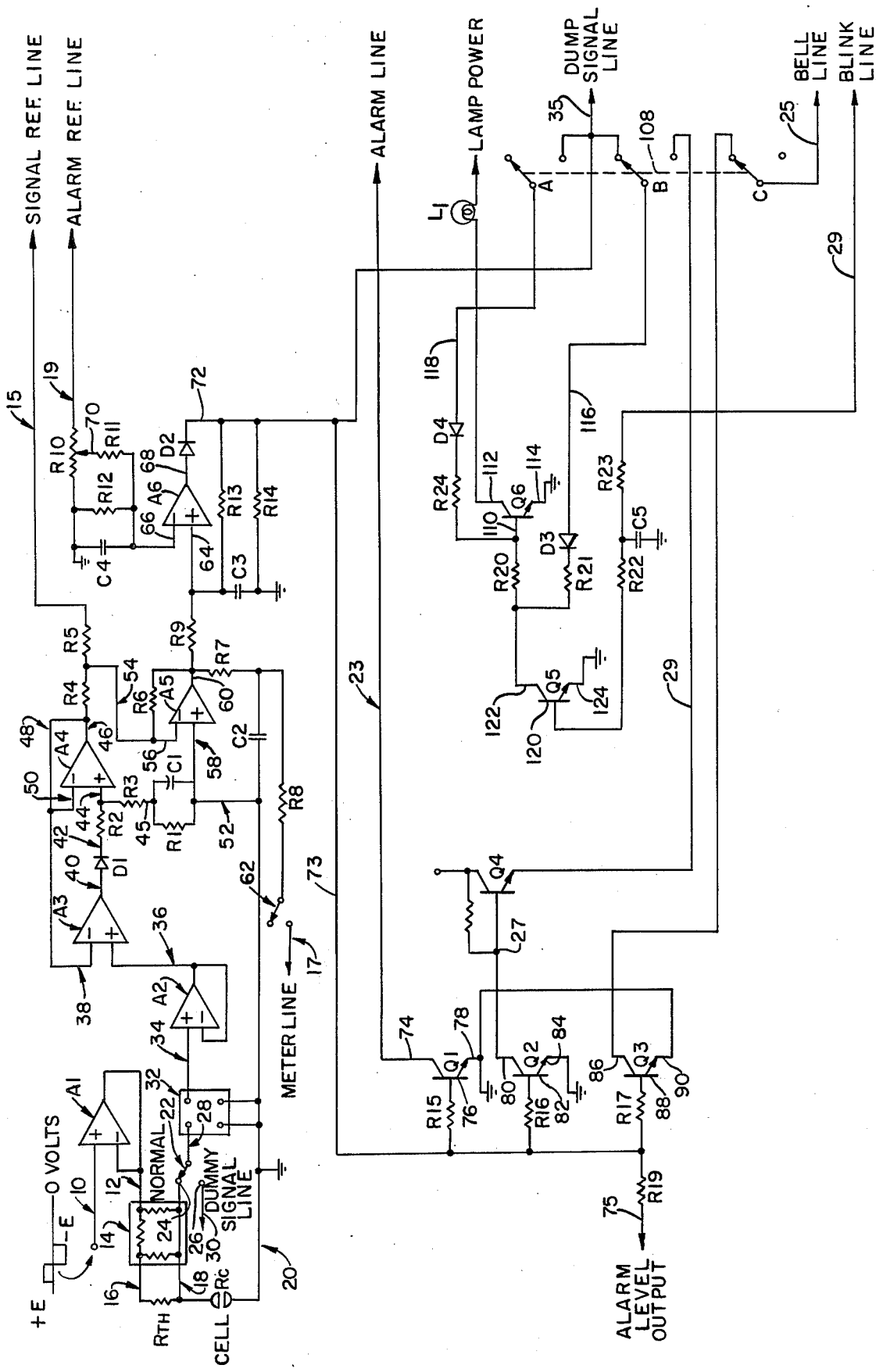
FIG. 1 is a schematic diagram of a salinity module.

Referring now to the drawings, FIG. 1 is a schematic diagram of one of the salinity modules. The signal line 10 receives a semi-square-wave signal generated by the reference voltage circuit (FIG. 4) and conducts it to the salinity module. The signal is adjusted and regulated in amplitude to about ±6 volts centrally by the reference voltage circuit, but it is not capable of driving the salinity cells. Therefore, included in each salinity module, is a cell driver A1. The cell driver being connected in the voltage follower mode, provides a voltage amplification of unity and has a very low output impedance, e.g., much less than one ohm. Consequently, the signal presented to conductor 12 is equal in amplitude to that on signal line 10, regardless of the variable loading presented by the salinity cell.

The signal on conductor 12 is modified slightly by a changeable, plug-in resistive range element 14 as it passes to terminal 16 of the conductivity cell. The signal present at terminal 16 then divides between a thermistor resistance Rth and cell resistance Rc. The fraction of this signal, which appears across the cell, that is, between the conductor 18 and circuit common on ground at 20, is given by the relation $$\frac{Rc}{Rth + Rc} = \frac{1}{1 + \frac{Rth}{Rc}}$$

where Rc is the resistance of the solution between the cell electrodes and Rth is the resistance of the thermistor. The value of the fraction is seen to depend entirely on the ratio of Rth to Rc. Thus, a thermistor having the same temperature variation, expressed in percent, as the solution Rc, would make the ratio Rth to Rc independent of temperature. That is, the response of the instrument would be perfectly compensated for variations in solution temperature. Unfortunately, the temperature variation of commercially available thermistors is similar to, but not identical with that of solutions. However, by slightly modifying the resistance of the thermistor Rth by the fixed series and shunt resistors of the range element 14, it is found possible to improve the resultant temperature compensation to an acceptable level. Moreover, the use of easily interchangeable, plug-in range elements 14 permits the optimum compensation to be utilized for the specific measuring cell and salinity range in use.

The signal on conductor 18 passes to a terminal 24 of a switch 22. When switch 22 is contacting terminal 24, its normal position, the cell signal, that is, the signal present at conductor 18, is fed to conductor 28 and on into the salinity circuit. When, switch 22 is contacting terminal 26—switch 22 is manually depressed and automatically spring-returned to the normal position—a manually-controlled test signal, or dummy signal, is fed from conductor 30 into the salinity circuit to provide for a test and calibration mode of operation to be described hereinafter.

The cell signal at conductor 28 passes through a noise filter 32, which rejects electrical noise, i.e., interference, picked up by the cell cable, but which otherwise has a negligible effect on the cell signal. The signal passes from the filter to conductor 34 which is the input of an amplifier A2 connected to the voltage follower mode. As connected, amplifier A2 presents an extremely high input impedance, i.e., much greater than ten megohms, and, consequently, produces no loading effect on the signal. Moreover, voltage follower A2 reproduces essentially unchanged the signal presented to it by conductor 34.

The output from amplifier A2 is fed to the positive input 36 of operational amplifier A3, which comprises, along with operational amplifier A4 and the associated passive components, a precision peak actuated detector. Amplifier A3 has a negative input 38 and an output 40. The output 40 connects through a diode D1 to conductor 42 and resistor R2. Operational amplifier A4 is connected in the voltage follower mode so that it provides unity voltage amplification. Amplifier A4 has a positive input 44, a negative input 50, an output 46 and a feedback conductor 48 which connects output 46 to negative input 50. The negative input 38 of amplifier A3 is connected to the junction of amplifier input 50 and feedback conductor 48. The positive input 44 of amplifier A4 is connected to resistor R2 to form a junction to which is connected one terminal of a resistor R3. The other terminal 45 of resistor R3 is connected to a parallel combination of resistor R1 and capacitor C1, which, in turn, is connected through conductor 52 to circuit common 20.

Before describing the operation of the precision peak actuated detector, consider the operation of the circuit described thus far if diode D1 is not present. A loop comprising amplifier A3 and A4 having an input 36 and an output 46 is formed. This loop is a feedback amplifier with a voltage amplification of unity, from input 36 to output 46. Capacitor C1 only affects the circuit to the extent that it slows circuit response to changes in input signals.

Considering now the operation of the precision peak detector when diode D1 is present, the diode D1 will conduct when conventional positive current flows in the direction from conductor 40 toward conductor 42. This current will charge capacitor C1, increasing the voltage at conductor 45. The voltage at conductor 45 will be reproduced accurately by voltage follower A4 and fed back through conductor 48 to the negative insert 50 of amplifier A4. The one hundred percent feedback of the amplifier A4 output, which is effective while diode D1 is conducting, insures that the voltages at conductors 45, 44, and 46 are essentially identical. Resistors R2 and R3 are included to help stabilize the feedback operation, and resistor R1 is included as a discharge path for capacitor C1. Resistor R1 has a large resistance (about 1000 times larger than R3) so that the voltage at conductor 45 is essentially the same as the voltage at conductor 44, which, as noted above and for the conditions assumed, is the same as the voltage at the input conductor 36 and the output conductor 46 of the precision peak actuated detector.

When the input voltage at conductor 36 is rising, the voltage on capacitor C1 will rise by virtue of the current flow through diode D1. Whenever the input voltage is rising, therefore, diode D1 will conduct, and the output voltage at 46 will be substantially equal to the input voltage at 36.

When the input voltage at conductor 36 reaches a peak and begins to decline, the voltage on capacitor C1 cannot fall since this would require it to discharge into the output 40 of amplifier A3, which discharge is prevented by diode D1. The voltage at conductor 45, and at conductors 42 and 44 therefore remain at the previous peak value, except for slight leakages through resistor R1, diode D1 and slight current flow into amplifier A4, all of which can be minimized through the proper choice of these components. However, resistor R1 is designed to permit eventual discharge of capacitor C1 and eventual recovery of the circuit. Consequently, the output voltage of the precision peak detector circuit is accurately equal to the peak voltage of the input waveform.

Reference to FIG. 2, which illustrates a semi-square-wave and distortion thereof caused by different values of capacitance, will aid in an explanation of how the use of a semi-square-wave together with a peak actuated detector makes this salinity meter practically impervious to the effects of cable capacitance. Curve a shows the semi-square-wave signal unaffected by capacitance, while curves b, c and d show the effects of increasing amounts of capacitance. If these signals are applied to a detector which responds to the peak value of the signal, then it is apparent that signals a, b and c will result in essentially the same output from the detector, while only signal d will result in a significantly reduced output. That is, only a value of capacitance large enough to produce a gross deformation of the waveform will result in significant error. For a pure square wave the error is given by the quantity $\exp(-T/RC)$, where T is the duration of a half-cycle, R is the output resistance of the cell and C is the cable capacitance. For a semi-square-wave the error will be less than $\exp(-T/RC)$, so that this expression will always give a conservative estimate of the error. For a frequency of 60 Hz, T may be taken conservatively as 5 or 6 milliseconds, the total half period being 8.33 milliseconds, which yields the conclusion that the error will be less than 0.5% when the product of RC is less than 1 millisecond. The largest value of R is about 25,000 ohms—this worst case occurs at low values of salinity and low temperature, e.g., 0.5 ppm salinity and 40 degrees F—which permits C to be as high as 40,000 pF. As cable capacitance is typically 70 pF/foot, this permits a cable length of 570 feet with an error of no more than 0.5%. This error decreases rapidly for shorter cable lengths, e.g., 0.25% at 500 feet; 0.1% at 430 feet; 0.01% at 330 feet. These cable lengths are considerably longer than those ordinarily encountered.

Referring again to FIG. 1, the signal at output 46, derived as discussed above, is the voltage across the cell electrodes. This cell signal will increase as the resistance of the water increases, i.e., as the salinity decreases. However, as it is generally desirable to utilize a signal which increases with salinity, it is necessary to alter this cell signal. This is accomplished by deriving the signal between conductor 12 and conductor 18, rather than the previously obtained cell signal between conductor 18 and conductor 20. The desired signal is given by the relation:

$$V_{12,18} = V_{12,20} - V_{18,20}$$

Concerning this equation, a distinction must be made between the square wave signals present at the actual conductors numbered 12, 18 and 20, and the d.c. voltages derived from these square waves by precision peak actuated detectors, these d.c. voltages being accurately equal to the peak value of the respective square waves. It is these d.c. voltages which are referred to in the equation last above.

The signal $V_{18,20}$ has been derived and is present at output conductor 46; to obtain $V_{12,18}$ it is only necessary to derive $V_{12,20}$ and perform the indicated substraction. The voltage $V_{12,20}$ is obtained by applying the semi-square-wave signal which is applied to the cell at conductor 12, to a precision peak detector identical to the one described above. Of course, this voltage, $V_{12,20}$, will be derived only once for the instrument, rather than individually for each salinity module. The precision peak detector which performs this function is located for convenience in the reference voltage circuit (FIG. 4); the resultant signal is reversed in sign by an operational amplifier having a gain of minus unity, thus producing the desired voltage, $-V_{12,20}$, which is distributed to each of the salinity modules on the signal reference line or conductor 15.

The signal $V_{18,20}$ present on conductor 46 and the signal $-V_{12,20}$ present on conductor 15 are added by accurately matched resistors R4 and R5, producing, in effect, the sum of $V_{18,20} - V_{12,20}$. This sum is fed through conductor 54 to the negative input 56 of a difference amplifier A5. The positive input 58 of amplifier A5 is connected to circuit common through conductor 52, while the amplifier output 60 is connected through resistor R6 to its negative input 56. Resistor R6 has been accurately matched to R4 and R5 to provide an accurate amplification of minus one, to produce the desired result of $V_{12,20} - V_{18,20} = V_{12,18}$ at output conductor 60. This circuit constitutes an accurate difference amplifier, and the signal at conductor 60 is the desired salinity signal.

The accurate salinity signal produced at conductor 60 may be used for the two functions which must be performed by the salinity monitoring instrument; the actuation of a meter to read salinity, and the actuation of alarm circuits when the salinity signal exceeds a preset valve.

The metering function is accomplished by connecting output conductor 60 through Resistors R7 and R8, and a read meter switch 62 to a meter line 17 and to the meter (not shown). In this way, a single, common meter can be used with individual read meter switches 62 on each module to produce a meter deflection corresponding to salinity signals of the respective modules. The meter resistance, R7+R8, is split and indicated, so that the bypass capacitor C2 may be used. Capacitor C2 isolates the operational amplifier A5 from the possible effects of interfering signals picked up by the meter line 17. This possibility exists as meter line 17 will normally be incorporated into a cable with many other conductors, which carry a variety of signals and power supply voltages.

The alarm function is accomplished by the use of an alarm circuit which compares the salinity signal on conductor 60 with a preset d.c. alarm reference voltage. The output conductor 60 is connected through resistor 9 to the positive input 64 of amplifier (comparator) A6, while also has a negative input 66 and an output 68. Input 64 is connected through capacitor C3 to circuit common. Input 66 is connected through a capacitor C4 to circuit common and a resistor R12 is connected in parallel with capacitor C4. A potentiometer resistance R10 is connected between one junction of C4 and R12 and alarm reference line 19, while the potentiometer arm 70 is connected through a resistor R11 to the negative input 66.

Since the salinity signal is capable of varying between zero and the peak value V12,20 of the semi-square-wave, the preset alarm reference signal should be capable of being varied between these same limits. To accomplish this, the voltage V12,20, already derived by means of a precision peak detector in the reference voltage circuit (FIG. 4), which is common to each salinity module, is buffered by a voltage follower amplifier (having unity amplification) and distributed to all the salinity modules on the alarm reference line 19. This alarm reference voltage appearing on conductor 19 is not reversed in polarity as is the signal reference voltage which appears on conductor 15, but the two are equal in magnitude. The alarm reference voltage is reduced to the desired magnitude by potentiometer R10, and is applied through resistor R11 to the negative input 66 of comparator A6. The salinity signal present on output conductor 60 is also fed through resistor R9 to comparator A6 at its positive input 64, so that comparator A6 functions as follows:

When the water quality is satisfactory, the salinity signal at input 64 will, by design, be less than the preset voltage at input 66, so that the output voltage at output 68 will be low. With certain choices of specific circuit conditions, this output voltage will, in fact, be negative. A diode D2 is connected to output conductor 68 and, since a negative output voltage cannot be conducted through diode D2, the resultant output voltage from the comparator circuit, at conductor 72, will be zero. Regardless of the specific circuit design, therefore, the voltage at conductor 72 will be zero so long as the water quality is satisfactory.

When there is an alarm condition, i.e., when water quality is unsatisfactory and of a high salinity, and, therefore, a high conductivity is present, the salinity signal at conductor 64 will be greater than the preset voltage at conductor 66, i.e., greater than the alarm level. When this condition exists, the comparator A6 will react with a high output voltage, approximating the positive supply voltage of comparator A6 at conductors 68 and 72. A small component of this voltage will be fed back to the input 64 of comparator A6 through a high resistance R13, which is about 100 times larger than R9. This feedback signal will reinforce the high salinity signal which caused the output voltage of the comparator to rise, and insures that the output voltage at conductor 72 will not decrease until the salinity signal drops by a definite step below the alarm level. The magnitude of this step is fed-back component and the purpose of introducing this step is to make the change from a non-alarm condition to an alarm condition, and vice versa, definite; that is, to eliminate repeated switching back and forth, from off to on, when the salinity signal fluctuates only slightly in the vicinity of the alarm point.

The alarm signal present at conductor 72, i.e., a high voltage for an alarm condition and a low or zero voltage for a non-alarm condition, performs several functions including remote alarm indication. When the alarm signal on conductor 72 is low or zero, i.e., a non-alarm condition, transistors Q1, Q2 and Q3 are all cut-off and non-conducting. Transistor Q1 has its collector 74 connected to the alarm line 23; this line, 23, is connected to the collectors or corresponding transistors in each of the other salinity modules. Normally, in the absence of an alarm condition in any of the modules, all of the Q1 transistors will be cut-off and the alarm will be unaffected by them. Under these circumstances, transistor Q8, FIG. 3, whose base is controlled by the alarm line 23, will conduct because of a current supplied to its base 92 through a resistor 18. Because of the conducting state of transistor Q8, an alarm relay RL1 will be energized, which is the normal, or non-alarm, condition of this relay.

This mode of operation, whereby relay RL1 is energized in the non-alarm state, is preferred because it provides the feature of fail-safe protection. Thus, a failure of the relay RL1, such as might be caused by an open relay coil, causes the relay to revert to its deenergized state and to activate an alarm device or indicator which will call attention to the defect. The contacts 104 on relay RL1 are brought out to external terminals to provide the option of using them for external alarm indication. The result is that an alarm condition in any one or more of the salinity modules, or a corresponding condition in the alarm latch circuit as described below concerning FIG. 6, will cause the alarm relay to change to its alarm state and provide an alarm indication at the external terminals.

With continuing reference to FIGS. 1 and 3, the instrument includes the features of a bell and bell control circuitry. The bell 106 is controlled by a bell relay RL2. Transistor Q9 in the bell circuit functions in the same manner as transistor Q8 in the remote alarm circuit just described, with the exception that a bell cutout switch 108 is included in each salinity module. When the bell cutout switch 108 is in its normal position or state, as shown in FIG. 1, the bell circuit is identical to the remote alarm circuit just described. When the bell cutout switch 108 of a given module is in its thrown or cutout state, the transistor Q3 of that module is isolated from the bell line 25, and, consequently, the module in question cannot cause bell activation, while the other modules retain the capability to actuate the bell. Thus, the salinity instrument includes the feature that an alarm condition in any one, or more, of the salinity modules, all of whose bell cutout switches are in the normal position, will cause the bell to ring, while any salinity module whose cutout switch is in the cutout position will lose that capability as long as the cutout switch is in that position.

The alarm signal present on conductor 72 is fed through conductor 73, resistor R19 and brought out at conductor 75 for the convenience of the user of the instrument. Resistor 19 must be of appropriate magnitude so that no passive load that may be connected to conductor 75, including a short circuit, will interfere with the operation of the instrument.

The salinity instrument provides each module with an alarm indication, through a blinking lamp, when the salinity level monitored by that module exceeds a preset valve. Each module has an alarm indication lamp L1, FIG. 1, on its front panel. Lamp L1 is illuminated when a transistor Q6 is conducting, which is the case when there is a drive signal at its base 110. This drive signal can be provided by one or two possible sources, conductors 116 or 118. With the bell cutout switch 108 in the normal position as shown in FIG. 1, this drive signal can only come from conductor 116, which is connected through section B of switch 108 to conductor 72, which carries the alarm signal. When conductor 72 is at zero, or low, voltage, i.e., no alarm signal is present, there is no possibility of a drive signal being provided to the base 110 of transistor Q6, so that Q6 will not conduct and alarm lamp L1 will not illuminate. This is the desired indication for the condition under consideration. The indications for the several possible operations conditions are summarized in Table 1 below. The situation discussed immediately above is case A in table 1:

| Salinity | Bell Cutout Switch Position | |
|---|---|---|
| Condition | Normal | Cutout |
| No Alarm | a. Off | c. Blinking |
| Alarm | b. Blinking | d. On |

The blinking mode is accomplished through a slow, about 4 Hz, square-wave-signal which is distributed through the instrument on a blink line conductor 29. The base 120 of the transistor Q5 is connected to the blink line 29 through resistors R22 and R23, while a capacitor C5 connects the junction between resistors R22 and R23 to circuit common. This 4 Hz squarewave, which is generated in the voltage reference circuit, FIG. 4, is constantly operating and has essentially equal on and off periods of about one-eighth second each. Its voltage in the on state is positive at about 13 volts, while in the off state it is zero volts. When the blink voltage is zero, transistor Q5 does not conduct, and thus has no effect on the circuit. When the blink voltage is positive, transistor Q5 will conduct and essentially short-circuit any signal present on conductor 122, conducted from 116, through Q5 collector 122 and emitter 124 to circuit common.

Circuit elements R22, R23, and C5 constitute a low-pass filter, introduced to slow down the transitions of the square wave, in order to reduce electromagnetic interference that may be caused by such transitions. Transistor Q5 will not, however, significantly affect any signal from conductor 118, because of the interposed resistor R20. Thus for Case b, Table 1, the alarm signal on conductor 72 will reach conductor 116 through section B of switch 108, and will be intermittently short-circuited at the blink frequency by transistor Q5 as described above. As a result, the conduction of transistor Q6 will be modulated by the blink wave, and the alarm lamp L1, which is connected in the collector circuit 112 of transistor Q6 will blink.

Cases c and d of Table 1 are satisfied as follows: With the bell cutout switch 108 thrown to the cutout position (not shown), any alarm signal present on conductor 72 will reach conductor 118 through section A of the switch to cause transistor Q6 to conduct, unaffected by the blink switching of transistor Q5. Lamp L1 will, therefore, be turned on, corresponding to Case d of Table 1.

To fulfill Case C of Table 1, there must be no alarm signal on conductor 72, so that no signal will reach transistor Q6 through conductor 118. However, a signal will reach transistor Q6 through conductor 116, which is connected to conductor 29 by section B of switch 108. The signal on conductor 29 is the reverse of the alarm signal on conductor 72, as transistor Q2 functions as a complementing circuit, while transistor Q4 is simply an emitter follower which supplies the signal on conductor 27 to conductor 29. That is, when there is no alarm signal on conductor 72, transistor Q2 will not conduct and the voltage at conductors 27 and 29 will be high; when there is an alarm signal on conductor 72, transistor Q2 will conduct, making the voltage at conductors 27 and 29 essentially zero. Referring now to Case c of Table 1, when there is no alarm signal on conductor 72, there will be a positive voltage on conductors 29 and 116 (through section B of switch 108). This signal on conductor 116 will be modulated by transistor Q5, as described above, thereby causing lamp L1 to blink as required. The diodes D3 and D4 are included to prevent improper interaction of parts of the circuit by restricting the direction of condution in the respective conductors.

As described above, the alarm indication is given by the blinking of a lamp, typically red, on the front panel of the salinity module, by the actuation of local and/or remote bells and by the lighting of a remote lamp. The bell cutout switch is provided to silience the local and remote bells. When the bell cutout switch is in the cutout position, the alarm lamp indication is modified from blinking to full on; if the excess salinity condition which resulted in the alarm condition should disappear with the switch in the cutout position, the indication reverts to blinking. The intention of this arrangement is to remind the operator to throw the switch back to the normal position. That is, the only fully normal lamp indication (fully normal in the sense that there is no alarm condition, and the cutout switch is in the normal position) is that in which the lamp is extinguished.

Referring now to FIG. 4, the basic square wave signal is generated by applying a 60 Hz voltage of about 30 volts to input 130 and, through current limiting resistor R25, to zener diodes D5 and D6. The result is a semi-square-wave signal of stabilized amplitude at conductor 132. The semi-square-wave signal is reduced to the desired magnitude through adjustment of the calibration rheostat R26, which, in effect, acts as a voltage divider in conjunction with the load presented by the dummy signal control. The result is to produce an adjusted semi-square-wave at conductor 10, which is identical with the signal line 10 discussed in reference to FIG. 1 above. The signal voltage present on conductor 10 drives the positive input 134 of amplifier A7, which, along with amplifier A8, comprises a precision peak detector identical to the one appearing in FIG. 1 and described above. The present peak detector produces a d.c. voltage at conductor 135 equal to the peak value of the full signal voltage on conductor 10. This d.c. voltage is then accurately reversed in sign by operational amplifier A9, which uses matched resistors R27 and R28, to yield the signal reference voltage on conductor 15. This signal reference voltage is utilized in the difference amplifiers, A5, of the salinity modules, as described above in relation to FIG. 1.

The full signal voltage is also reproduced accurately, without reversal of sign, by the voltage follower amplifier A10 for distribution to each of the salinity modules on the alarm reference line 19, as discussed above in relation to FIG. 1.

The salinity instrument also provides a dump feature whereby, when a salinity module detects an alarm condition indicating excessive impurity in the water stream being monitored, a relay cuts off power to a solenoid valve to cause the valve to open and dump the impure water. The alarm signal on conductor 72 of each salinity module is brought out from each module by a direct connection through dump signal line 35 (FIG. 1) so it will be available for connection to a dump circuit. Normally, it is contemplated that only a minority of the salinity modules in any instrument will be connected to dump circuits, but each module is capable of such connection. Moreover, when these salinity modules are physically designed as plug-in units, they may be made identical in construction and used interchangeably. The feature of dump connection is determined in the instrument, rather than in the salinity modules themselves, which feature provides clear advantages for production and use.

Each dump valve which is controlled by the instrument has an associated indicator lamp on the front panel of the instrument; these lamps are normally fully illuminated, and switch to a blinking mode when its associated valve is dumping. FIGS. 5 and 6 illustrate the interrelation between the lamp switching circuits and the lamp circuits. In the normal, or non-dumping state, the dump valve switch 136 and the dump relay 138 are positioned as illustrated, i.e., normally closed and deenergized, respectively. A 115 VAC power supply (not shown) applied at inputs 140 produces a current flow through dump valve switch 136, dump valve coil 142, conductor 144, dump relay 138 and conductor 146 to maintain the dump valve 148 in the energized, non-dumping state.

When a dump condition occurs, a positive dump signal is present on conductor 35, as described in relation to FIG. 1 above. This dump signal is transmitted by emitter follower Q7, essentially unchanged, to transistor Q15, which then conducts and energizes the dump relay 138, thereby causing the dump relay contact to open. The conduction path for the dump valve coil 142 is thus broken, and the dump valve 148 reverts to its deenergized or dumping state. The dump valve switch 136 then supplies power supplied at inputs 140 to the conductor 150. This means that even when the dump signal at conductor 35 disappears, i.e., a condition of zero voltage of conductor 35, non-conductance by transistor Q15 and the dump relay coil 139 and a reclosing of dump relay switch 138, the dump valve coil 142 will not be restored to its energized condition because the dump valve switch 136 will still be open. Restoration of current in the dump valve coil 142 requires both the disappearance of the dump signal on conductor 35, and manual resetting of the dump valve switch 136.

When a dump condition exists, the 115 VAC power is applied to the optical relay 152 through inputs 140 and conductors 150 and 154. Resistor R29 limits the current to the optical relay 152, while diode D8 and resistor R30 protect the optical relay from the negative half-cycle of the 115 VAC power. When power is thus applied to the optical relay 152, resistor R31 responds by dropping to a low value of resistance. This causes the voltage on conductor 156 to drop to a low value, in turn causing a Schmidt trigger, transistors Q10 and Q14, to change state; voltage at conductor 158 goes to a high value, while the voltage at conductors 160 and 162 goes to a low value, cutting off transistor Q11. When transistor Q11 is cut off, the blink square wave on conductor 29 can pass to transistor Q12, alternately short-circuiting the drive current fed through resistor R34 to the base 164 of transistor Q13, and permitting this drive current to reach the base 164. This sets up a blinking signal on conductor 166 which is fed to the appropriate valve position indicator (VPI) lamp (FIG. 6), causing it to blink.

Normally, when the dump valve 148 is in its non-dumping condition, no power is applied to optical relay 152 (FIG. 5), so that conductors 156 and 160 are at a high voltage causing zener diode D9 to conduct and maintain transistor Q11 in a conducting state. The use of a Schmidt trigger and zener diode, rather than a more basic circuit, assures a definite transition from a conducting to a non-conducting state, and vice-versa, in transistor Q11. When transistor Q11 is conducting, the blink square wave supplied on conductor 29 is short-circuited at the base of transistor Q12, ensuring that Q12 is constantly cut off. Drive current supplied through resistor R34 to the base of transistor Q13 can therefore pass without interruption, and the VPI lamp will be continuously on.

Referring now to FIG. 6, there is illustrated a circuit used to combine all of the voltages at the VPI lamps into one signal which is applied to the alarm line 23. The result is that a dump indication in any one, or more, of the lamps grounds the alarm line 23 in the same manner that an alarm indication does. The remote alarm indication discussed above is therefore an alarm/dump indication.

When there is no dump condition present, the Q13 transistor (FIG. 5) for each dump channel is constantly conducting, i.e., all of the VPI lamps are constantly illuminated so that conductors 168, 170 and 172 (FIG. 6) are all at essentially zero potential. Diodes D10, D11 and D12 all cut off so that the voltage at conductor 174 is zero. Conductor 176 is therefore at a high voltage, while conductor 178 is at a low voltage. Thus, zener diode D13 is cut off, producing a zero potential at conductor 180. Transistor Q18 is, consequently, cut off, and has no effect on the alarm line 23.

The situation described above is reversed when even one VPI lamp is blinking, that is, when even one dump valve is dumping. Assume that VPI lamp 1 is blinking. This means that during the illuminated phase of the blink cycle, the voltage on conductor 168 is still zero but, during the dark phase, transistor Q13 is cut off so that the full positive lamp supply voltage passes through the lamp and appears at conductor 168. This positive voltage can pass through diode D10 and charge capacitor C6, which is designed large enough to hold this charge during the full blink cycle. Conductor 182 is therefore positive for the full blink cycle, making conductor 176 low in voltage and conductors 178 and 180 high in voltage. Transistors Q16 and Q17 constitute a Schmidt trigger, as described above concerning transistors Q10 and Q14 in FIG. 5. This Schmidt trigger together with zener diode D13 assures a positive transition between the two states of the circuit. This is particularly advantageous in this case because capacitor C6 holds the voltage on conductor 182 only approximately constant over the blink cycle. With conductor 180 at a high voltage, transistor Q18 conducts and grounds the alarm line 23. Transistor Q18 thus serves the same function for dump indication that Q1 (FIG. 1) serves for alarm indication, that is, to ground the alarm line 23 and produce a remote alarm indication.

With continuing reference to FIG. 6, the power lamp 184 is conditioned to blink when the dummy signal potentiometer switch 186 is not positioned at the counterclockwise terminal 188. In its normal position, the dummy signal potentiometer switch 186 is fully counterclockwise and contacting terminal 188 as illustrated. Positive voltage supplied by a power source (not shown) on conductor 190 can pass to conductor 192, causing transistor Q19 to conduct and, thereby, grounding the blink square wave on conductor 194 to turn off transistor Q20. A drive current can then pass through resistor R33 to the base 196 of transistor Q21 causing it to conduct. Power indicator lamp 184 will then illuminate because of a current flow through a path including lamp 184, conductor 198 and transistor Q21.

However, when the dummy potentiometer switch 186 is open, or contacting terminal 189, there is no voltage on conductor 192, so that transistor Q19 is cut off. The blink square wave present on conductor 194 can then pass to transistor Q20 turning it on and off at the frequency of the blink square wave. During the periods that transistor Q20 is turned on, the drive current supplied to the base 196 of transistor Q21 is shorted to ground so that transistor Q21 is alternately turned on and off at the frequency of the blink square wave. Since transistor Q21 is in the circuit of the power indicator lamp 184, it will blink.

It can thus be seen that the present invention provides a novel device for monitoring the salinity of solutions.

Obviously many modifications and variations of the present invention are possible in the light of the above teachings. It is therefore to be understood that within the scope of the appended claims the invention may be practiced otherwise than as specifically described.

What is claimed is:

1. A circuit for monitoring the salinity of a solution comprising
   a conductivity cell;
   a temperature compensating resistor connected in series with said cell;
   signal source means supplying a semi-square-wave signal to said cell and said resistor in series such that a cell output signal proportional to the conductivity of the solution is produced with said cell output signal having a peak amplitude;
   amplifier means having a high input impedance receiving said cell output signal; and
   peak actuated detector means receiving said cell output signal from said amplifier means including signal storage means for receiving and storing said cell output signal, unidirectional conducting means supplying said cell output signal to said signal storage means and means responsive to the peak amplitude of said cell output signal stored by said signal storage means to generate a salinity signal proportional to the conductivity of the solution whereby said salinity ssignal is substantially unaffected by stray capacitance due to the use of said semi-square-wave signal and said peak actuated detector means.

2. The invention as recited in claim 1 further comprising a meter line and switch means for selectively connecting said salinity signal to said meter line.

3. The invention as recited in claim 1 further comprising alarm reference signal generating means for generating a variable alarm reference signal; and comparator means for comparing said salinity signal to said alarm reference signal to generate an alarm signal whenever said salinity signal exceeds said alarm reference signal.

4. The invention as recited in claim 3 further comprising an alarm lamp; an alarm bell; and an alarm signal control circuit for receiving said alarm signal to cause actuation of said alarm lamp and said alarm bell.

5. The invention recited in claim 4 further comprising a bell cutout switch for selectively eliminating said alarm bell from said alarm signal control circuit.

6. The invention recited in claim 3 further comprising a solenoid valve controlled by said alarm signal control circuit whereby said solenoid valve causes dumping of said solution upon the appearance of said alarm signal.

7. The invention recited in claim 6 further comprising dump lamp means connected in said alarm signal control circuit for producing a visible blinking signal while said solenoid valve is in a dump state.

8. The invention as recited in claim 3 further comprising a test signal generating means for generating a test signal; and switch means connected between said cell and said high impedance means whereby said cell signal and said test signal may be selectively fed to said high impedance means.

9. The invention as recited in claim 8 further comprising a lamp means connected in said alarm signal control circuit for providing a blinking indication during periods when said test signal is fed to said high impedance means.

* * * * *